United States Patent
Kitamura et al.

(10) Patent No.: US 10,732,133 B2
(45) Date of Patent: Aug. 4, 2020

(54) X-RAY IMAGING SYSTEM CONTAINING X-RAY APPARATUS HAVING GRATINGS AND OBJECT HOUSING FOR SETTING ENVIRONMENTAL CONDITION INDEPENDENT OF EXTERNAL ENVIRONMENT

(71) Applicant: Konica Minolta, Inc., Tokyo (JP)

(72) Inventors: Mitsuharu Kitamura, Tokyo (JP); Yasunori Tsuboi, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 16/194,928

(22) Filed: Nov. 19, 2018

(65) Prior Publication Data

US 2019/0170668 A1 Jun. 6, 2019

(30) Foreign Application Priority Data

Dec. 4, 2017 (JP) ................................ 2017-232242

(51) Int. Cl.
*G01N 23/041* (2018.01)
*G06T 11/00* (2006.01)

(52) U.S. Cl.
CPC .......... *G01N 23/041* (2018.02); *G06T 11/003* (2013.01); *G01N 2223/31* (2013.01); *G01N 2223/3103* (2013.01); *G01N 2223/3106* (2013.01); *G01N 2223/401* (2013.01)

(58) Field of Classification Search
CPC ....... A61B 6/04; A61B 6/0407; A61B 6/0421; A61B 6/4035; A61B 6/42; A61B 6/4208; A61B 6/4291; A61B 6/484; A61B 6/508; A61B 6/045; A61B 6/40; A61B 6/4233; A61B 6/44; A61B 6/4429; A61B 6/4435; G01N 23/041; G01N 2223/31; G01N 2223/3106; G01N 2223/3103
USPC .............................. 378/36, 62, 204, 208, 209
See application file for complete search history.

(56) References Cited

U.S. PATENT DOCUMENTS

| | | | |
|---|---|---|---|
| 8,041,004 B2 * | 10/2011 | David | A61B 6/484 378/36 |
| 8,602,648 B1 * | 12/2013 | Jacobsen | G21K 7/00 378/208 |
| 8,855,265 B2 * | 10/2014 | Engel | A61B 6/00 378/36 |
| 9,084,528 B2 * | 7/2015 | Geller | A61B 6/00 |
| 9,107,638 B2 * | 8/2015 | Hoshino | A61B 6/484 |
| 9,330,456 B2 * | 5/2016 | Sperl | G06T 7/0012 |

(Continued)

FOREIGN PATENT DOCUMENTS

JP 4445397 B2 1/2010

*Primary Examiner* — Allen C. Ho
(74) *Attorney, Agent, or Firm* — Lucas & Mercanti, LLP (57) ABSTRACT

An X-ray imaging system including: an X-ray Talbot imaging apparatus which is provided with an object table, an X-ray source, a plurality of gratings, and an X-ray detector side by side in a direction of an X-ray radiation axis, and irradiates the X-ray detector with an X-ray from the X-ray source through an object and the plurality of gratings to obtain a moire image required for forming a reconstruction image of the object; and an object housing inside which the object is housed and an environmental condition independent of an external environment is set, wherein the object housing is provided detachably with respect to the object table.

11 Claims, 6 Drawing Sheets

(56) References Cited

U.S. PATENT DOCUMENTS

| | | | | |
|---|---|---|---|---|
| 9,538,970 B2 * | 1/2017 | Koehler | ................. | A61B 6/482 |
| 9,572,541 B2 * | 2/2017 | Hoshino | ............... | A61B 6/5217 |
| 9,629,600 B2 * | 4/2017 | Hoshino | ................ | A61B 6/484 |
| 9,719,947 B2 * | 8/2017 | Yun | ................. | G01N 23/20075 |
| 9,775,575 B2 * | 10/2017 | Proksa | ................ | G01N 23/046 |
| 9,855,018 B2 * | 1/2018 | Hamano | .............. | A61B 6/4233 |
| 9,872,660 B2 * | 1/2018 | Hamano | ................ | A61B 6/484 |
| 9,874,531 B2 * | 1/2018 | Yun | ................. | G01N 23/20075 |
| 9,916,655 B2 * | 3/2018 | Stampanoni | ........... | A61B 6/483 |
| 10,172,580 B2 * | 1/2019 | Roessl | ................ | A61B 6/4291 |
| 10,349,908 B2 * | 7/2019 | Yun | ...................... | A61B 6/4291 |
| 10,359,375 B2 * | 7/2019 | Cao | ........................ | G21K 1/025 |
| 10,365,235 B2 * | 7/2019 | Tanabe | ................ | A61B 6/5235 |
| 10,514,342 B2 * | 12/2019 | Kagias | ................ | A61B 6/4035 |

* cited by examiner

X-RAY IMAGING SYSTEM CONTAINING X-RAY APPARATUS HAVING GRATINGS AND OBJECT HOUSING FOR SETTING ENVIRONMENTAL CONDITION INDEPENDENT OF EXTERNAL ENVIRONMENT

BACKGROUND

Technological Field

The present invention relates to an X-ray imaging system provided with an X-ray Talbot imaging apparatus.

Description of the Related Art

As a conventional X-ray imaging apparatus, one that includes a Talbot interferometer or a Talbot-Lau interferometer having a plurality of gratings (hereinafter referred to as "X-ray Talbot imaging apparatus") is known. In order to obtain a high-resolution reconstruction image by an X-ray Talbot imaging apparatus, a fringe scanning technique is employed (for example, refer to JP 4445397 B1). In the fringe scanning technique, one of the plurality of gratings is shifted in a direction of a slit pitch in increments of 1/M (M is a positive integer, where M>2 in an absorption image, and M>3 in a differential phase image and a small-angle scattering image) of the slit pitch of the grating, whereby performing reconstruction with an image (moire image) imaged M times. The Fourier transform may also be employed. In the Fourier transform, with the presence of an object, one moire image is imaged by an X-ray Talbot imaging apparatus, and in the image processing, the moire image is subjected to the Fourier transform or the like, whereby reconstructing a differential phase image or the like.

In recent years, such an X-ray Talbot imaging apparatus is required for observing an internal mechanism of a test object (or an object).

If an internal mechanism of an object is observed while the object is placed under any environmental conditions, it is possible to check changes in the object under a predetermined environmental condition. Especially, observing the progress in normal times and under stringent environmental conditions makes it possible to see the changing mechanism of the object as a substance. Simultaneously capturing such conditions in a differential phase image or a small-angle scattering image specifically imaged by an X-ray Talbot imaging apparatus and in an ordinary absorption image offers an advantage in explaining a phenomenon which is not observed in a test or inspection in the related art.

However, a plurality of gratings, a main part of the X-ray Talbot imaging apparatus, has a grating structure with a pitch of several μm, and significant environmental changes cause minute deformation in the gratings, parts that hold the gratings or the like. This may cause noise or the like in a reconstruction image to be formed. In the meantime, many objects to be subjected to non-destructive testing require, for example, imaging of states under a special temperature and humidity and imaging of states associated with environmental changes. Therefore, a change in environment of an object without changing an installation environment of only an X-ray Talbot imaging apparatus brings a great advantage to the X-ray Talbot imaging apparatus.

SUMMARY

An object of the present invention is to prevent troubles in an X-ray Talbot imaging apparatus attributed to an installation environment and to clarify an internal mechanism of an object which is not observed in a test or inspection in the related art.

To achieve at least one of the abovementioned objects, according to an aspect of the present invention, an X-ray imaging system reflecting one aspect of the present invention includes: an X-ray Talbot imaging apparatus which is provided with an object table, an X-ray source, a plurality of gratings, and an X-ray detector side by side in a direction of an X-ray radiation axis, and irradiates the X-ray detector with an X-ray from the X-ray source through an object and the plurality of gratings to obtain a moire image required for forming a reconstruction image of the object; and an object housing inside which the object is housed and an environmental condition independent of an external environment is set, wherein the object housing is provided detachably with respect to the object table.

BRIEF DESCRIPTION OF THE DRAWINGS

The advantages and features provided by one or more embodiments of the invention will become more fully understood from the detailed description given hereinafter and the appended drawings which are given by way of illustration only, and thus are not intended as a definition of the limits of the present invention, and wherein.

DETAILED DESCRIPTION OF THE EMBODIMENTS

Hereinafter, one or more embodiments of the present invention will be described in detail with reference to the drawings. The following embodiment includes various technically preferable limitations in order to carry out the present invention. However, the technical scope of the present invention is not limited to the following embodiment and illustrated examples.

In an X-ray imaging system described in this embodiment, the interior of an object housing 30 that houses an object H is set to an environmental condition independent of an external environment, and the object H is imaged with an X-ray Talbot imaging apparatus 1. Accordingly, the X-ray imaging system herein enables imaging of the object H under environmental conditions different from normal times.

The object H in this embodiment represents all kinds of samples such as metals, resin, composite materials, and woven fabric, and includes all kinds of subjects that required examination of internal properties. Imaging with the X-ray Talbot imaging apparatus 1 enables observation of an internal mechanism of the object H.

In this embodiment, as the X-ray Talbot imaging apparatus 1, one that includes a Talbot-Lau interferometer provided with a source grating (also referred to as "multi-grating", "multi-slit", "G0 grating", or the like) 12 is employed. An X-ray Talbot imaging apparatus 1 including a Talbot interferometer provided with only a first grating (also referred to as "G1 grating") 14 and a second grating (also referred to as "G2 grating") 15 instead of the source grating 12 may also be employed.

[X-ray Talbot Imaging Apparatus]

Figure 1:
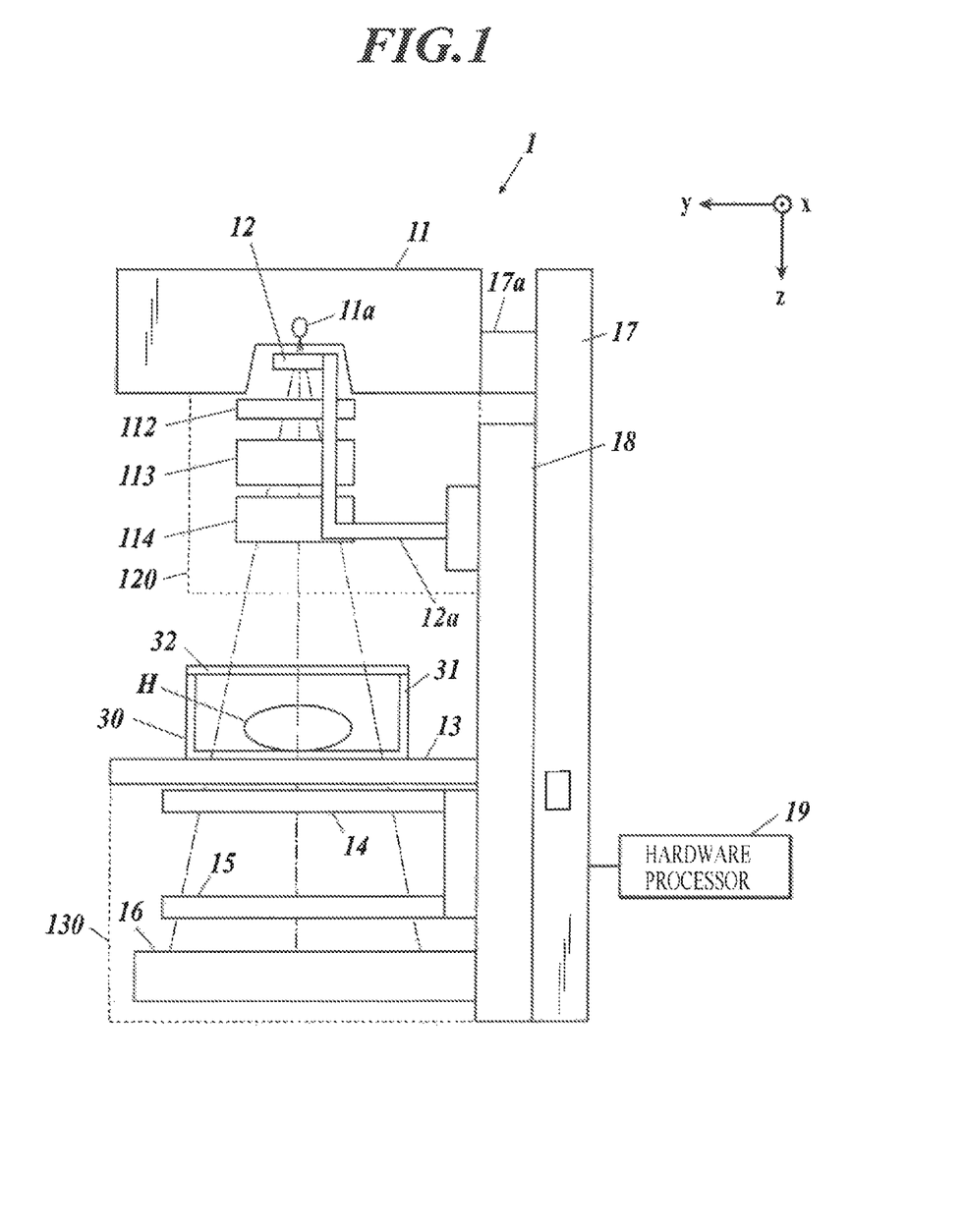
FIG. 1 is a schematic view showing an overall picture of an X-ray Talbot imaging apparatus and an object housing.

FIG. 1 is a schematic view showing an overall picture of the X-ray Talbot imaging apparatus 1 and the object housing 30.

The X-ray Talbot imaging apparatus 1 according to this embodiment includes an X-ray generator 11, the source grating 12, an object table 13, the first grating 14, the second grating 15, an X-ray detector 16, a support 17, and abase 18.

According to such an X-ray Talbot imaging apparatus 1, a moire image of the object H disposed at a predetermined position with respect to the object table 13 is imaged by a method based on the principle of a fringe scanning technique, or the moire image is analyzed by the Fourier transform, so that at least three types of images are reconstructed (referred to as "reconstruction images"). The three types of images are an absorption image (the same as an ordinary X-ray absorption image) obtained by imaging an average component of moire fringes in the moire image, a differential phase image obtained by imaging phase information of the moire fringes, and a small-angle scattering image obtained by imaging visibility of the moire fringes. Resynthesis or the like of these three types of reconstruction images may form more kinds of images.

The fringe scanning technique is a method to obtain a high-resolution reconstruction image by shifting one of a plurality of gratings in a direction of a slit pitch in increments of 1/M (M is a positive integer, where M>2 in an absorption image, and M>3 in a differential phase image and a small-angle scattering image) of the slit pitch of the grating, and by performing reconstruction with a moire image imaged M times.

The Fourier transform is a method to reconstruct and form a differential phase image or the like by imaging one moire image with an X-ray Talbot imaging apparatus 1, with the presence of an object H, and by performing the Fourier transform or the like on the moire image during the image processing.

First, the principle common to a Talbot interferometer and a Talbot-Lau interferometer will be described with reference to FIG. 2.

Figure 2:
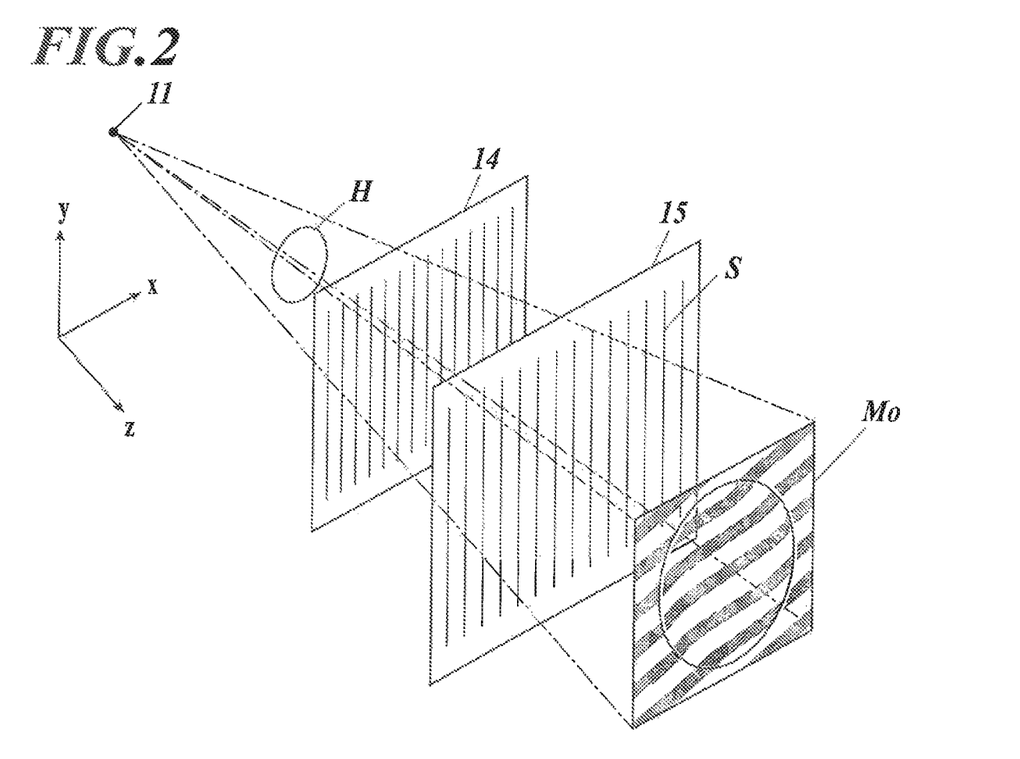
FIG. 2 is a view for explaining the principle of a Talbot interferometer.

FIG. 2 shows a case where a Talbot interferometer is employed. Note that a case where a Talbot-Lau interferometer is employed is described basically similarly. The z direction in FIG. 2 corresponds to the vertical direction in the X-ray Talbot imaging apparatus 1 of FIG. 1, the x and y directions in FIG. 2 correspond to the horizontal directions (front-back, right-left directions) in the X-ray Talbot imaging apparatus 1 of FIG. 1.

Figure 3:
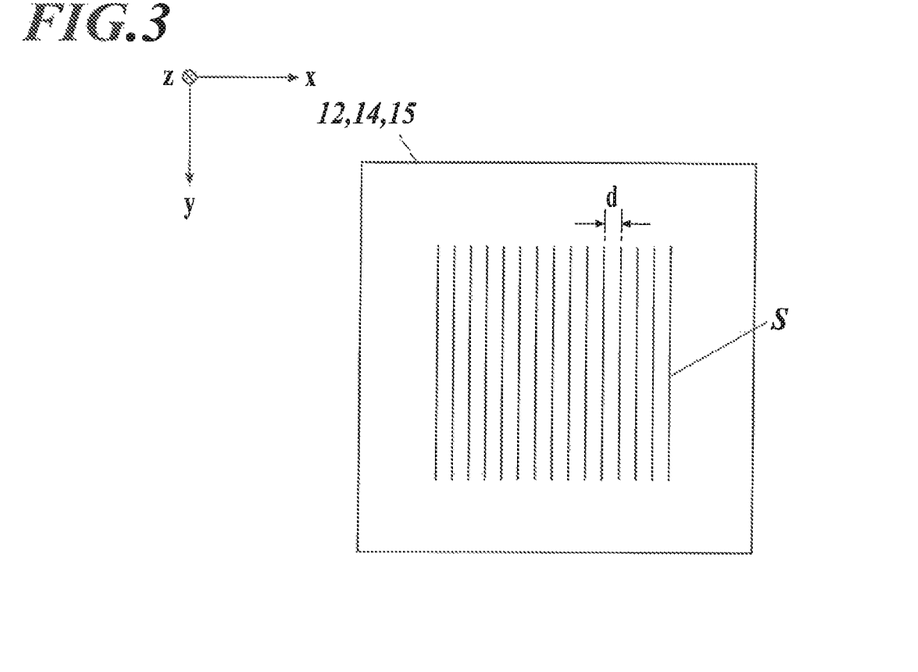
FIG. 3 is a schematic plan view of a source grating, a first grating, and a second grating.

As shown in FIG. 3, the first grating 14 and the second grating 15 (as well as the source grating 12 in a Talbot-Lau interferometer) include a plurality of slits S arranged at a predetermined pitch d in the x direction perpendicular to the z direction which is a direction of X-ray radiation.

As shown in FIG. 2, an X-ray emitted from an X-ray generator 11 is transmitted through the first grating 14 (in a Talbot-Lau interferometer, the X-ray emitted from the X-ray generator 11 is converted to multiple light by the source grating 12 (not shown in FIG. 2)). The transmitted X-ray forms an image at a constant interval in the z direction. This image is called "self-image" (also referred to as "grating image" or the like), and a phenomenon in which a self-image is formed at a constant interval in the z direction is called "Talbot effect".

In other words, the Talbot effect indicates a phenomenon in which coherent light penetrates the first grating 14 provided with the slits S at the constant pitch d, as shown in FIG. 3, causing the light to form a self-image at a constant interval in a light traveling direction.

As shown in FIG. 2, the second grating 15 provided with slits S, as in the first grating 14, is disposed at a position where a self-image of the first grating 14 is formed. When the second grating 15 is arranged in such a manner that an extending direction of the slits S of the second grating 15 (that is, the x-axial direction in FIG. 2) becomes substantially parallel to an extending direction of the slits S of the first grating 14, a moire image Mo is obtained on the second grating 15.

In FIG. 2, if the moire image Mo is drawn on the second grating 15, moire fringes and the slits S are mixed up, making the drawing complicated. Therefore, the moire image Mo is drawn as being separated from the second grating 15. However, actually, the moire image Mo is formed on the second grating 15 and downstream of the second grating 15. The moire image Mo is imaged by the X-ray detector 16 disposed immediately below the second grating 15.

As shown in FIGS. 1 and 2, when the object H is present between the X-ray source 11a and the first grating 14, the phase of the X-ray is shifted due to the object H. This phase shift wobbles the moire fringes of the moire image Mo from the edge of the object H. On the other hand, if the object H is not present between the X-ray source 11a and the first grating 14, which is not shown in the drawing, the moire image Mo with only the moire fringes shows up. This is the principle of a Talbot interferometer and a Talbot-Lau interferometer.

Based on this principle, in the X-ray Talbot imaging apparatus 1 according to this embodiment, as shown in FIG. 1, for example, the second grating 15 is disposed at a position inside a second cover unit 130 where the self-image of the first grating 14 is formed. As described above, separating the second grating 15 and the X-ray detector 16 blurs the moire image Mo (see FIG. 2). Therefore, in this embodiment, the X-ray detector 16 is disposed immediately below the second grating 15. The second grating 15 may be formed of an emitting material such as a scintillator or amorphous selenium, and the second grating 15 may be formed in an integrated manner with the X-ray detector 16.

The second cover unit 130 is provided to protect the first grating 14, the second grating 15, the X-ray detector 16, and the like so that somebody or something does not hit or touch the X-ray detector 16 and the like.

Although not shown in the drawing, the X-ray detector 16 includes conversion elements that generate electric signals depending on emitted X-rays. The conversion elements are arranged two-dimensionally (in matrix form), and the electric signals generated by the conversion elements are read as image signals. In this embodiment, the X-ray detector 16 is configured to image the moire image Mo, or the X-ray image formed on the second grating 15, as an image signal for each conversion element. The pixel size of the X-ray detector 16 is 10 to 300 (µm), and preferably, 50 to 200 (µm).

An example of the X-ray detector 16 may include a flat panel detector (FPD). There are an indirect conversion FPD that converts a detected X-ray into an electric signal through a photoelectric conversion element; and a direct conversion FPD that directly converts a detected X-ray into an electric signal. Either FPD is employable.

In an indirect conversion FPD, photoelectric conversion elements that form a pixel are two-dimensionally arranged together with a thin film transistor (TFT) under a scintillator plate made of CsI, Gd2O2S, or the like. When an X-ray incident on the X-ray detector 16 is absorbed by the scintillator plate, the scintillator plate emits light. This emitted light leads to accumulation of charges in each photoelectric conversion element, and the accumulated charges are read out as image signals.

In a direct conversion FPD, an amorphous selenium film having a film thickness of 100 to 1000 (μm) is formed on glass by thermal evaporation of amorphous selenium, and the amorphous selenium film and electrodes are evaporated on an array of the two-dimensionally arranged TFT. When the amorphous selenium film absorbs an X-ray, a voltage is liberated in the substance in the form of electron-hole pairs, and a voltage signal between the electrodes is read by the TFT.

Imaging units such as a charge coupled device (CCD) and an X-ray camera may also be used as the X-ray detector 16.

In this embodiment, the X-ray Talbot imaging apparatus 1 images a plurality of moire images Mo by what is called a fringe scanning technique. In other words, the X-ray Talbot imaging apparatus 1 according to this embodiment images the plurality of moire images Mo by shifting relative positions of the first grating 14 and the second grating 15 in the x-axial direction in FIGS. 1 to 3 (that is, a direction perpendicular to the extending direction of the slits S (y-axial direction)).

An image processing device (not shown) which has received image signals of the plurality of moire images Mo from the X-ray Talbot imaging apparatus 1 executes image processing and reconstructs an absorption image, a differential phase image, a small-angle scattering image, and the like based on the plurality of moire images Mo.

Therefore, in order to image the plurality of moire images Mo by the fringe scanning technique, the X-ray Talbot imaging apparatus 1 according to this embodiment may move the first grating 14 in the x-axial direction in increments of a predetermined amount. The X-ray Talbot imaging apparatus 1 may move the second grating 15, instead of the first grating 14, or may move both gratings in the x-axial direction.

While fixing the relative positions of the first grating 14 and the second grating 15, the X-ray Talbot imaging apparatus 1 may image one moire image Mo, and this moire image Mo may be analyzed by the Fourier transform in the image processing executed by the image processing device to reconstruct an absorption image, a differential phase image, and the like.

Hereinafter described is configurations of other parts in the X-ray Talbot imaging apparatus 1 according to this embodiment. The X-ray Talbot imaging apparatus 1 in this embodiment is of what is called vertical type and includes the X-ray generator 11, the source grating 12, the object table 13, the first grating 14, the second grating 15, and the X-ray detector 16 arranged in this order in the z direction or the gravity direction. In other words, in this embodiment, the z direction is the direction of X-ray radiation from the X-ray generator 11.

As the X-ray source 11a, the X-ray generator 11 includes, for example, a Coolidge X-ray source, a rotating anode X-ray source or the like, either of which is widely and generally used in a medical field. Other X-ray sources may also be employed herein. The X-ray generator 11 in this embodiment emits an X-ray in a cone-beam shape from a focal point. In other words, as shown in FIG. 1, the X-ray is emitted in such a manner that the X-ray spreads out as it separates from the X-ray generator 11, centering on an X-ray radiation axis Ca that coincides with the z direction (that is, an X-ray radiation range).

In this embodiment, the source grating 12 is provided below the X-ray generator 11. In regard to vibration of the X-ray generator 11 caused by rotation of an anode in the X-ray source 11a, in order not to transmit the vibration to the source grating 12, the source grating 12 in this embodiment is not attached to the X-ray generator 11 but to a fixing member 12a that is attached to the base 18 provided on the support 17.

In this embodiment, in order to prevent propagation of the vibration of the X-ray generator 11 to other parts of the X-ray Talbot imaging apparatus 1 such as the support 17 (or to reduce the vibration to be propagated), a cushioning member 17a is provided between the X-ray generator 11 and the support 17.

In this embodiment, in addition to the source grating 12, to the fixing member 12a, attached are a filter (also referred to as "additional filter") 112 that changes the quality of an X-ray transmitted through the source grating 12, a beam limiting device 113 that limits an irradiation field of an X-ray to be emitted, and an irradiation field lamp 114 that irradiates an object with visible light instead of an X-ray before X-ray radiation so as to adjust a position of the X-ray.

The source grating 12, the filter 112, and the beam limiting device 113 are not necessarily disposed in this order. Furthermore, in this embodiment, a first cover unit 120 that protects the source grating 12 and the like is disposed around those members.

In this embodiment, the hardware processor 19 (see FIG. 1) includes a computer in which a central processing unit (CPU), a read only memory (ROM), a random access memory (RAM), an input/output interface, and the like are connected to each other by a bus (those members are not shown in the drawing). Instead of a general-purpose computer as in this embodiment, the hardware processor 19 may include a dedicated control device. Although not shown in the drawing, the hardware processor 19 is provided with appropriate units and devices such as an input unit and an output unit including an operation unit, a storage unit, and a communication unit.

The output unit includes a display unit (not shown) that displays information necessary for performing various operations of the X-ray Talbot imaging apparatus 1 and displays a formed reconstruction image.

The hardware processor 19 performs overall control of the X-ray Talbot imaging apparatus 1. In other words, for example, the hardware processor 19 is connected to the X-ray generator 11 and may set a tube voltage, a tube current, an irradiation time, and the like in the X-ray source 11a. The hardware processor 19, for example, may also be configured to relay transmission and reception of signals and data between the X-ray detector 16 and an external image processing device (not shown).

In other words, the hardware processor 19 in this embodiment functions as a controller that causes a series of imaging to acquire the plurality of moire images Mo (one moire image in the Fourier transform) necessary for forming a reconstruction image of the object H.

[Object Housing]

As shown in FIG. 1, the object housing 30 is a box-like body that internally houses the object H, and the interior of the object housing 30 may be set to an environmental condition independent of an external environment.

Figure 4A:
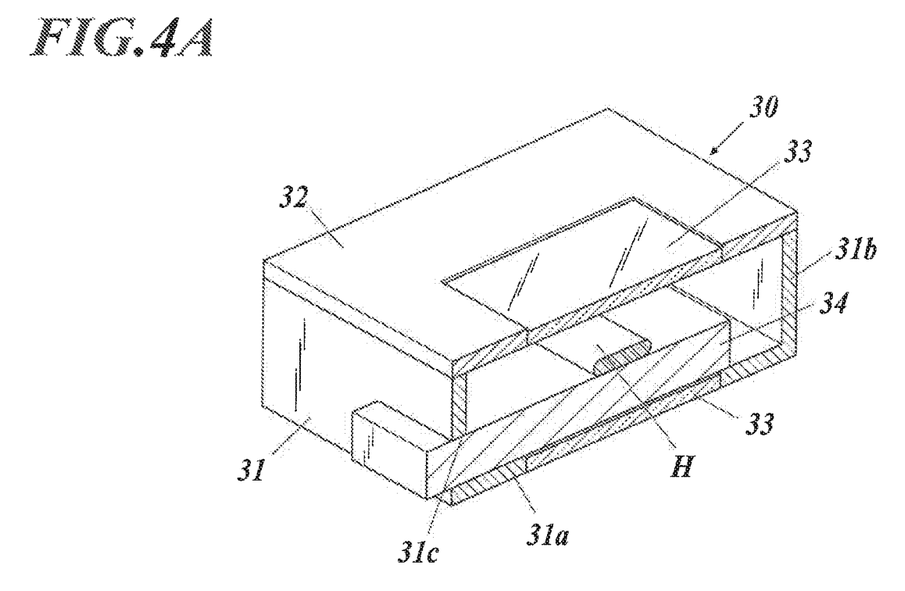
FIGS. 4A and 4B are cross-sectional perspective views each showing a configuration of the object housing.
Figure 4B:
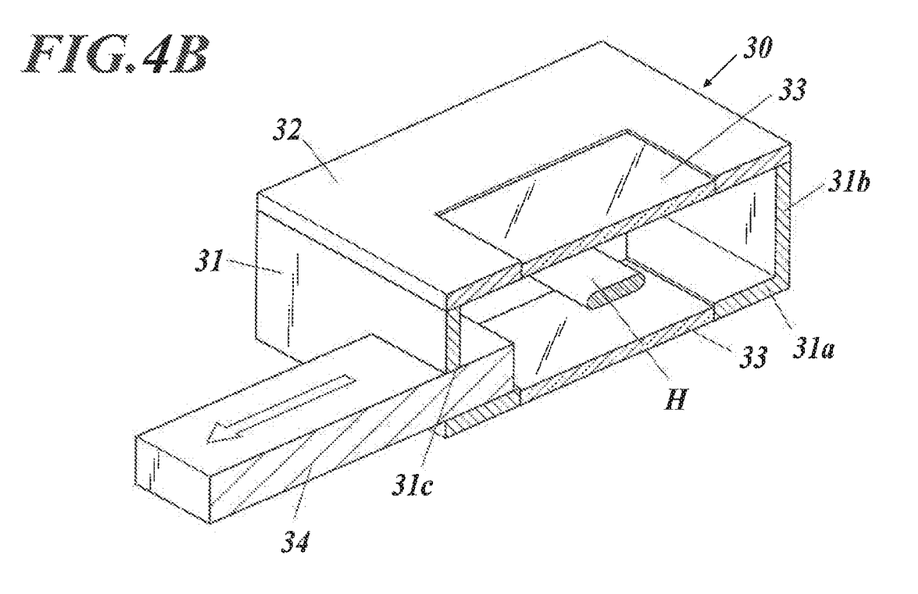

As shown in FIGS. 4A and 4B, the object housing 30 includes a box-shaped main body 31 provided with a bottom 31a and a peripheral wall 31b, and a cover 32 that covers an opening of the main body 31.

With the opening of the main body 31 being covered with the cover 32, the interior of the object housing 30 is hermetically sealed.

Using such an object housing 30, the periphery of the object H may be set to the environmental condition independent of the external environment.

The cover 32 is provided detachably with respect to an upper end of the main body 31.

A structure for attaching or detaching the cover 32 to or from the upper end of the main body 31 is not particularly limited. It is preferable to employ, for example, a connecting fitting (not shown) called a toggle latch or a patch fitting, or a fixing screw (not shown) that fixes the cover 32 to the upper end of the main body 31.

With the cover 32 being attached to the upper end of the main body 31, the object housing 30 functions as a pressure-resistant (or explosion-proof) box-shaped body.

Each of the main body 31 and the cover 32 includes an X-ray transmitter 33 on the X-ray radiation axis Ca and in the X-ray radiation range around the X-ray radiation axis Ca. The X-ray transmitter 33 is less likely to hinder transmission of X-rays compared to peripheral parts. The X-ray transmitter 33 includes a material having high X-ray transmissivity (for example, resin or resin mixed with carbon fiber or glass fiber).

The X-ray transmitter 33 of the main body 31 is provided in the bottom 31a. Since the X-ray from the X-ray generator 11 is emitted in a cone-beam shape as described above, the X-ray transmitter 33 in the main body 31 may be provided in an area wider than the X-ray transmitter 33 in the cover 32.

In this embodiment, the main body 31 and the cover 32, excluding the X-ray transmitter 33, are mainly made of metal, but those members may be made of a material with high X-ray transmissivity.

Examples of environmental conditions independent of an external environment inside the object housing 30 include conditions related to temperature and/or humidity inside the object housing 30. In other words, in this embodiment, temperature and/or humidity are examples of environmental conditions independent of an external environment inside the object housing 30, and the temperature and/or humidity inside the object housing 30 are adjustable.

In order to adjust the temperature inside the object housing 30, the object housing 30 further includes a heater unit 34 as shown in FIGS. 4A and 4B. Accordingly, the temperature inside the object housing 30 may be set to any temperature.

The adjustment of the temperature in the heater unit 34 may be automatically controlled by the hardware processor 19 (controller) of the X-ray Talbot imaging apparatus 1 in conjunction with the X-ray Talbot imaging apparatus 1.

In other words, the hardware processor 19 controls the series of imaging performed by the X-ray Talbot imaging apparatus 1 to acquire the plurality of moire images Mo, and at the time of the series of imaging, the hardware processor 19 may also adjust the temperature inside the object housing 30. That is, the hardware processor 19 and the heater unit 34 are communicably connected to each other.

As shown in FIGS. 4A and 4B, the heater unit 34 in this embodiment may be put in and out from the object housing 30.

In the peripheral wall 31b of the main body 31, the object housing 30 includes an inlet/outlet port 31c that allows the heater unit 34 to be put in and out of the object housing 30.

In this embodiment, the operation of putting in and out the heater unit 34 may be automatically controlled by the hardware processor 19 (controller) of the X-ray Talbot imaging apparatus 1 in conjunction with the X-ray Talbot imaging apparatus 1.

In other words, in the series of imaging by the X-ray Talbot imaging apparatus 1, the heater unit 34 may be put in and out by the hardware processor 19. That is, the hardware processor 19 and a drive unit that drives the heater unit 34 are communicably connected to each other.

Humidity inside the object housing 30 is adjusted by, for example, a humidity adjustment unit (not shown) having functions of humidification and dehumidification. The operation of this humidity adjustment unit may be also automatically controlled by the hardware processor 19 (controller) of the X-ray Talbot imaging apparatus 1 in conjunction with the X-ray Talbot imaging apparatus 1.

The object housing 30 and the X-ray Talbot imaging apparatus 1 are mechanically independent from each other, and the object housing 30 is detachably disposed in the object table 13 in the X-ray Talbot imaging apparatus 1. More specifically, the main body 31 of the object housing 30 is attached to the object table 13. However, the present invention is not limited to this configuration, and both the main body 31 and the cover 32 may be attached to any part of the X-ray Talbot imaging apparatus 1.

In this embodiment, although not shown in the drawing, an engagement unit is provided between a lower end of the main body 31 and the object table 13. Example of such an engagement unit includes a simple structure that facilitates attachment and detachment such as the aforementioned connecting fitting and fixing screw. In addition, the object housing 30 may include a holding unit that holds the edge of the object table 13. Alternatively, the object table 13 may include a holding unit that holds the object housing 30. The object housing 30 is desirably attached to or detached from the object table 13 by a simple operation such as sliding or lifting in the x direction, the y direction, or a rotation direction.

If the interior of the object housing 30 is set to a high temperature, for example, the object housing 30 itself may be heated. Even in such a case, detaching the object housing 30 from the object table 13 reduces an influence of environmental changes on the X-ray Talbot imaging apparatus 1. As needed, X-ray Talbot imaging is carried out with the object housing 30 being attached to the object table 13. Accordingly, it is possible to clarify an internal mechanism of an object which is not observed in a test or inspection in the related art.

In X-ray Talbot imaging using the object housing 30, for example, the object H may be housed in the object housing 30, and then, an environmental condition inside the object housing 30 may be gradually changed to another condition different from an external environment. Alternatively, an environmental condition inside the object housing 30 may be changed to another condition different from an external environment, and then, the object H may be housed in the object housing 30 to see changes over time. Furthermore, environmental conditions inside the object housing 30 may be changed at some interval.

[Configuration Example 1 of Object Housing]

The object housing 30 is not necessarily used for each imaging. When ordinary X-ray Talbot imaging and X-ray Talbot imaging in a state where the interior of the object housing 30 is set to an environmental condition independent of an external environment are simultaneously performed, it is possible to acquire highly accurate information on the object H. The ordinary X-ray Talbot imaging and the X-ray Talbot imaging in a state where the interior of the object housing 30 is set to an independent environmental condition are frequently performed by turns in some cases.

Figure 5A:
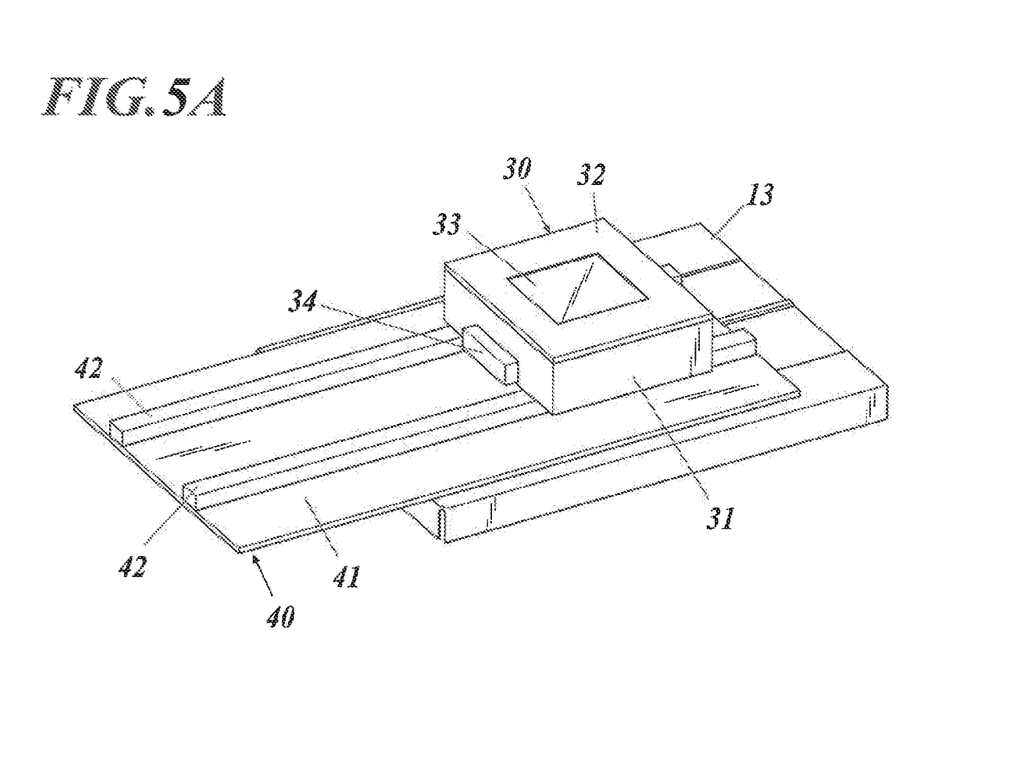
FIGS. 5A and 5B are schematic views each showing a configuration of a moving system that moves the object housing.
Figure 5B:
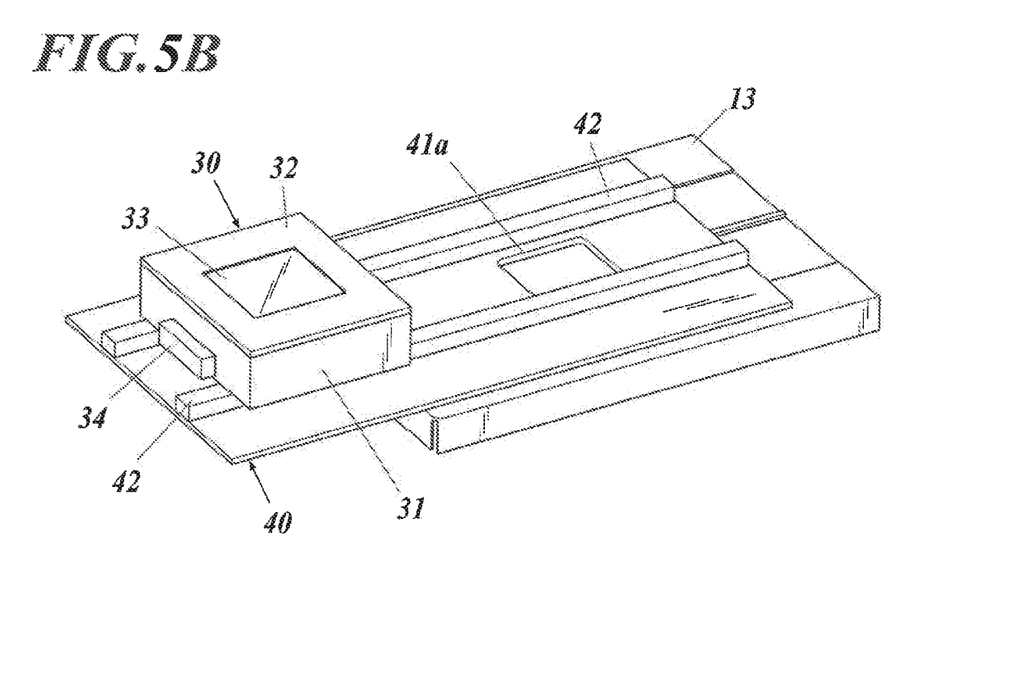

Therefore, as shown in FIGS. 5A and 5B, the object housing 30 is provided on the object table 13 of the X-ray Talbot imaging apparatus 1, being movable back and forth with respect to the X-ray radiation range. In other words, the object housing 30 is provided on the object table 13 of the X-ray Talbot imaging apparatus 1 so as to be able to advance and retreat with respect to the X-ray radiation range.

The object table 13 is provided with a moving system 40 that moves the object housing 30 so that the object housing 30 moves away from or closer to the X-ray radiation range.

The moving system 40 includes a stand 41 attached to the object table 13 and a guide rail 42 elongated along a length direction of the stand 41.

The stand 41 is formed in a rectangular plate shape and is set to have a length protruding outward beyond the upper surface of the object table 13. In addition, an opening 41a corresponding to the X-ray radiation range is formed at a portion of the stand 41 placed on the upper surface of the object table 13, so that the stand 41 is less likely to hinder transmission of X-rays.

The guide rail 42 is provided on the stand 41 in pairs and elongated along the length direction of the stand 41. The guide rail 42 includes a movable body (not shown) that is movable along the guide rail and a drive unit (not shown) that causes the movable body to operate.

The object housing 30 is attached to the movable body of the guide rail 42 and moves (advances and retreats) from a position corresponding to the X-ray radiation range of the object table 13 to the outside of the object table 13.

Imaging is performed in a state shown in FIG. 5A when the object housing 30 is used, and imaging is performed in a state shown in FIG. 5B when the ordinary X-ray Talbot imaging is performed.

The operation of the movable body in the moving system 40 may be automatically controlled by the hardware processor 19 (controller) of the X-ray Talbot imaging apparatus 1 in conjunction with the X-ray Talbot imaging apparatus 1. That is, the hardware processor 19 and a drive unit that drives the movable body are communicably connected to each other.

[Configuration Example 2 of Object Housing]

Each of the plurality of gratings 12, 14, and 15 is a one-dimensional grating. Accordingly, a direction shows up in a moire image Mo acquired by the X-ray Talbot imaging apparatus 1. In other words, depending on an imaging direction of the object H, for example, a fiber direction and a scratch direction are visible in some portions and invisible in some portions.

Figure 6:
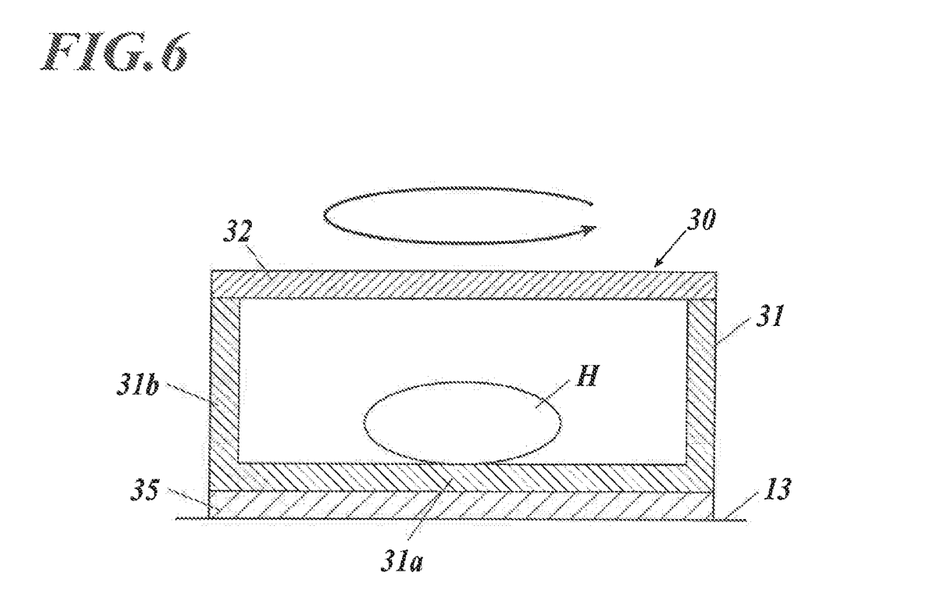
FIG. 6 is a schematic view of the object housing including a rotator.

Therefore, as shown in FIG. 6, one of the object table 13 and the object housing 30 of the X-ray Talbot imaging apparatus 1 includes a rotator 35 that rotates the object H about the X-ray radiation axis Ca. When the object housing 30 that houses the object H is rotated at any angle by the rotator 35, an image of the object H imaged before the rotation and an image of the object H imaged after the rotation are viewed differently, and a predetermined portion of the object H which is not viewed before the rotation becomes visible in the image that is imaged after the rotation.

Example of the rotator 35 in this embodiment includes a rotation member which has a circular or frame shape with an opening (not shown) formed at the center and of which a rotation center corresponds to the X-ray radiation axis Ca. The opening formed in the center corresponds to the X-ray transmitter 33 and easily transmits X-rays.

Similarly to the X-ray transmitter 33, the rotator 35 may include a material having high X-ray transmissivity. In this case, it is not necessary to form an opening in the center.

The rotator 35 is positioned between the object table 13 and the bottom 31a of the main body 31 in the object housing 30. A lower end face of the rotator 35 is attached to the object table 13, and an upper end face thereof is attached to the bottom 31a. The upper end face of the rotator 35 is provided with a rotating body (not shown) which is rotatable and to which the bottom 31a of the main body 31 in the object housing 30 is attached, and the lower end face of the rotator 35 is provided with a drive unit that rotates the rotating body.

In this embodiment, the object housing 30 is provided with the rotator 35, but the object table 13 of the X-ray Talbot imaging apparatus 1 may be provided with the rotator 35. Furthermore, the main body 31 of the object housing 30 may be provided with the rotator 35.

The rotation of the rotator 35 may be automatically controlled by the hardware processor 19 (controller) of the X-ray Talbot imaging apparatus 1 in conjunction with the X-ray Talbot imaging apparatus 1. That is, the hardware processor 19 and a drive unit that drives the rotating body are communicably connected to each other.

[Another Configuration Example of Object Housing]

The case where examples of environmental conditions independent of an external environment inside the object housing 30 include conditions related to temperature and/or humidity inside the object housing 30 has been described, but the environmental conditions are not limited thereto and may be modified appropriately.

In other words, for example, the interior of the object housing may be made vacuum, pressurized, or depressurized. Alternatively, the object H may be immersed in water, or the object H may be vibrated. Furthermore, various environmental conditions as described above including the conditions related to temperature and/or humidity may be used in combination.

Although not shown in the drawing, the object housing 30 is provided with appropriate equipment, devices, and the like for preparing various environmental conditions as described above.

In other words, in a case where the interior of the object housing 30 is made vacuum, pressurized, or depressurized, the object housing 30 is provided with a pump, a valve mechanism, or the like.

In a case where the object H is immersed in water, the object housing 30 is provided with a water storage tank and a water supply and drainage mechanism.

In a case where the object H is vibrated, the object housing 30 is provided with a vibrator together with a vibration isolating mechanism that prevents transmission of the vibration to the X-ray Talbot imaging apparatus 1.

Various equipment, devices, and the like for setting the interior of the object housing 30 to an environmental condition independent of an external environment may be automatically controlled by the hardware processor 19 (controller) of the X-ray Talbot imaging apparatus 1 in conjunction with the X-ray Talbot imaging apparatus 1.

As described above, according to this embodiment, it is possible to observe an internal mechanism of the object H when the object H is housed in the object housing 30 under any environmental condition, which enables observation of changes in a substance in each environment. Especially, observation of an environment in consideration with the usual usage environment and observation of the progress under stringent environmental conditions make it possible to observe the changing mechanism of the substance. In other words, simultaneously capturing any environmental condition of the object H in a differential phase image or a small-angle scattering image specific to a Talbot image and in an ordinary absorption image leads to clarification of the internal mechanism of the object H which is not observed in a test or inspection in the related art.

Furthermore, as described above, the plurality of gratings 12, 14 and 15 or a main member of the X-ray Talbot imaging apparatus 1 has a grating structure with a pitch of several μm. Therefore, with a significant environmental change, the gratings, parts that hold the gratings or the like are slightly deformed, which may cause noise or the like in a reconstruction image to be formed. In the meantime, many objects to be subjected to non-destructive testing require, for example, imaging of states under a special temperature and humidity and imaging of states associated with environmental changes. Since the object housing 30 is detachably attached to the object table 13, the object housing 30 may be attached to the object table 13 as necessary.

Therefore, it is possible to image the object H by the X-ray Talbot imaging apparatus 1 under an environmental condition independent of an external environment without changing an installation environment of the X-ray Talbot imaging apparatus 1, and to prevent troubles in the X-ray Talbot imaging apparatus 1 attributed to the installation environment, and to clarify the internal mechanism of the object H which is not observed in a test or inspection in the related art.

The X-ray Talbot imaging apparatus 1 includes the hardware processor (hardware processor 19) that causes the series of imaging for acquiring the plurality of moire images Mo necessary for forming a reconstruction image of the object H. The hardware processor of the X-ray Talbot imaging apparatus 1 may automatically control setting of independent environmental conditions inside the object housing 30 in conjunction with the X-ray Talbot imaging apparatus 1. Therefore, while controlling the imaging by the X-ray Talbot imaging apparatus 1, the hardware processor may appropriately control the interior of the object housing 30 to be set to an environmental condition independent of an external environment or to an environmental condition similar to the external environment. Such a configuration makes it easier to clarify the internal mechanism of the object H.

Since independent environmental conditions include conditions related to temperature and/or humidity inside the object housing 30, the interior of the object housing 30 may be set to a high temperature and high humidity, or to a low temperature and low humidity. Accordingly, the internal mechanism of the object H is observed while the object H is housed in the object housing 30 under such conditions.

On the X-ray radiation axis Ca and in the X-ray radiation range around the X-ray radiation axis Ca, the object housing 30 includes the X-ray transmitter 33 which is less likely to hinder transmission of X-rays compared to the peripheral parts. Therefore, by housing the object H at the position of the X-ray transmitter 33, it is easy to transmit X-rays at the time of imaging compared to a case where the object housing 30 does not house the object H at the position of the X-ray transmitter 33.

Each of the plurality of gratings 12, 14, and 15 is a one-dimensional grating. Therefore, by moving one of the plurality of gratings 12, 14, and 15 relative to other gratings to perform the fringe scanning technique, and by repeating imaging in which the X-ray detector 16 reads image signals in accordance with emitted X-rays, it is possible to acquire the plurality of moire images Mo necessary for forming a reconstruction image of the object H.

Furthermore, in consideration of the fact that each of the plurality of gratings 12, 14, 15 is a one-dimensional grating, one of the object table 13 and the object housing 30 of the X-ray Talbot imaging apparatus 1 includes the rotator that rotates the object H about the X-ray radiation axis Ca. Therefore, an image of the object H imaged before the rotation and an image of the object H imaged after the rotation are viewed differently, and a portion (for example, scratches, defects and the like) of the object H which is not viewed in the image before the rotation is observed in the image that is imaged after the rotation. Accordingly, the object H may be inspected in detail.

The X-ray Talbot imaging apparatus 1 and the object housing 30 are mechanically independent from each other. Therefore, the object housing 30 is easily attached to and detached from the object table 13. Accordingly, it is easy to attach the object housing 30 to the object table 13 as needed and to detach it from the object table 13.

The object housing 30 is disposed on the object table 13 of the X-ray Talbot imaging apparatus 1, being movable back and forth with respect to the X-ray radiation range. Therefore, it is possible to appropriately change conditions between the imaging carried out by the X-ray Talbot imaging apparatus 1 with the object housing 30 and the ordinary imaging carried out by the X-ray Talbot imaging apparatus 1 without the object housing 30.

[Modification]

The aforementioned embodiment illustrates the configuration in which the interior of the object housing 30 is set to an environmental condition independent of an external environment. The following modification illustrates a configuration that changes physical properties of the object H itself. The following modifications may be combined to the extent possible.

Similarly to the embodiment, the X-ray Talbot imaging apparatus 1 in the following modifications is configured to image a plurality of moire images Mo by what is called the fringe scanning technique. However, the X-ray Talbot imaging apparatus 1 herein may employ the Fourier transform in which one moire image is subjected to the Fourier transform and the like to reconstruct an image such as a differential phase image.

[Modification 1]

Figure 7:
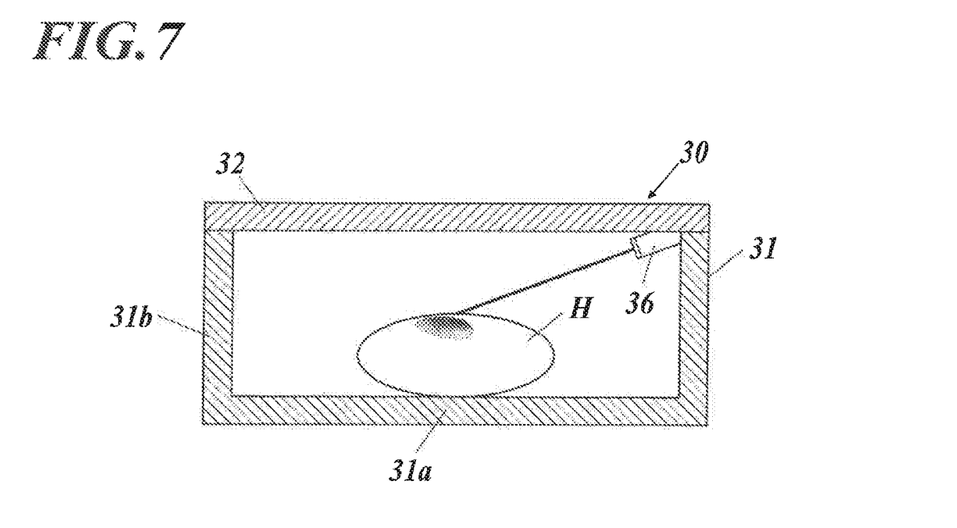
FIG. 7 is a schematic view of the object housing including a laser radiator.

As shown in FIG. 7, the object housing 30 in this modification has a laser radiator 36 that irradiates the object H with a laser beam.

Laser beams are excellent in directivity and convergence. Raising an output of a laser beam enables intensive heating of a minute portion in the object H.

The laser radiator 36 is provided inside the object housing 30, having an angle adjustable relative to the object H.

In regard to the adjustment of the angle and the radiation of a laser beam and/or operation of stopping the radiation of a laser beam, the laser radiator 36 may be automatically controlled by the hardware processor 19 (controller) of the X-ray Talbot imaging apparatus 1 in conjunction with the X-ray Talbot imaging apparatus 1.

In other words, the hardware processor 19 controls the series of imaging performed by the X-ray Talbot imaging apparatus 1 to acquire the plurality of moire images Mo, and at the time of the series of imaging, the hardware processor 19 also control each operation of the laser radiator 36. That is, the hardware processor 19 and the laser radiator 36 are communicably connected to each other.

A laser beam of the laser radiator 36 in this modification intensively heats the minute portion of the object H. Therefore, performing the X-ray Talbot imaging leads to clarification of the mechanism of partial changes in physical properties of the object H due to heating.

The output of the emitted laser beam may be considerably increased to partially destroy the object H, and the mechanism of changes in physical properties of the destroyed object H may be imaged by the X-ray Talbot imaging apparatus 1.

In order not to hinder X-ray irradiation of the X-ray generator 11 with respect to the object H, in this modification, a laser beam is emitted while the X-ray radiation is stopped.

When laser beam radiation is performed during the X-ray Talbot imaging, a laser beam is to be emitted toward a position not to hinder the X-ray irradiation with respect to the object H.

According to this modification, the object housing 30 includes the laser radiator 36 that irradiates the object H with a laser beam. Therefore, performing the X-ray Talbot imaging leads to clarification of the mechanism of partial changes in physical properties of the object H irradiated with the laser beam. Since such X-ray Talbot imaging is performed without changing an installation environment of the X-ray Talbot imaging apparatus 1, it is possible to prevent troubles in the X-ray Talbot imaging apparatus 1 attributed to the installation environment.

Furthermore, as described in the embodiment, the X-ray Talbot imaging apparatus 1 is preferable in that the X-ray Talbot imaging is performed while the interior of the object housing 30 is set to an environmental condition independent of an external environment and that the object H is imaged under various conditions.

[Modification 2]

Figure 8:
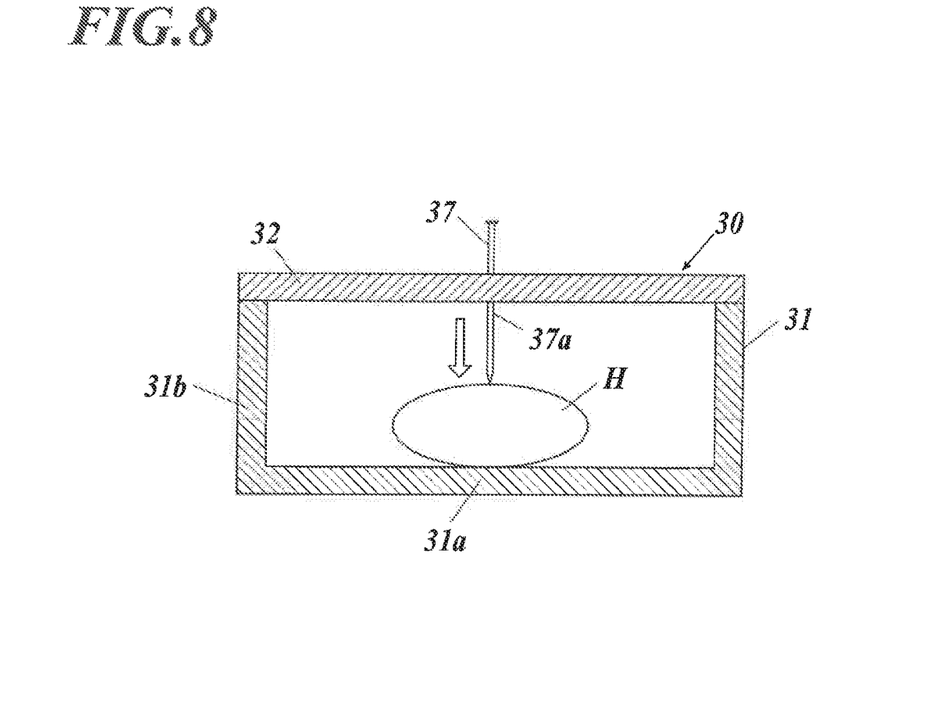
FIG. 8 is a schematic view of the object housing including a nail inserter.

As shown in FIG. 8, the object housing 30 in this modification includes a nail inserter 37 that performs a nailing test on the object H.

In the nailing test, an internal short circuit is simulated by piercing a nail in a thickness direction of an electrode body such as a lithium ion battery, and the degree of heat generation is studied to check the safeness of the battery. In the nailing test, when the nail penetrates a battery cell, an internal short circuit occurs between a positive electrode current collector and a negative electrode current collector in the battery cell through the nail, leading to a phenomenon of local heating of contact portions between these current collectors and the nail and the periphery of the contact portions.

The object housing 30 in this modification includes the nail inserter 37, so that it is possible to clarify an internal mechanism of a nailed portion in the object H.

The nail inserter 37 includes a nail body 37a, a through hole (not shown) for the nail body 37a formed in the cover 32 of the object housing 30, and a packing material (not shown) provided on the inner periphery of the through hole.

The packing material includes an elastically deformable material which ensures hermeticity of the object housing 30 when the nail body 37a is not penetrated through the through hole.

The nail body 37a may have a built-in temperature sensor for measuring the temperature inside the object H.

In this modification, the nail body 37a is inserted or removed by a user such as a radiological technician or an inspector, but the present invention is not limited thereto. The nail body 37a may be inserted or removed by a drive unit (not shown). In a case where the nail body 37a is inserted or removed by such a drive unit, the drive unit may be automatically controlled by the hardware processor 19 (controller) of the X-ray Talbot imaging apparatus 1 in conjunction with the X-ray Talbot imaging apparatus 1.

In the illustrated example, the nail body 37a is provided in a central portion of the object housing 30, but the invention is not limited thereto. The nail body 37a may be inserted or removed obliquely relative to the object H. Alternatively, the nail body 37a may be inserted or removed from the peripheral wall 31b side of the main body 31.

According to this modification, the object housing 30 includes the nail inserter 37 for performing the nailing test on the object H. Therefore, performing the X-ray Talbot imaging leads to clarification of the mechanism of changes in physical properties of the object H subjected to the nailing test. Since such X-ray Talbot imaging is performed without changing an installation environment of the X-ray Talbot imaging apparatus 1, it is possible to prevent troubles in the X-ray Talbot imaging apparatus 1 attributed to the installation environment.

Furthermore, as described in the embodiment, the X-ray Talbot imaging apparatus 1 is preferable in that the X-ray Talbot imaging is performed while the interior of the object housing 30 is set to an environmental condition independent of an external environment and that the object H is imaged under various conditions.

[Modification 3]

Figure 9:
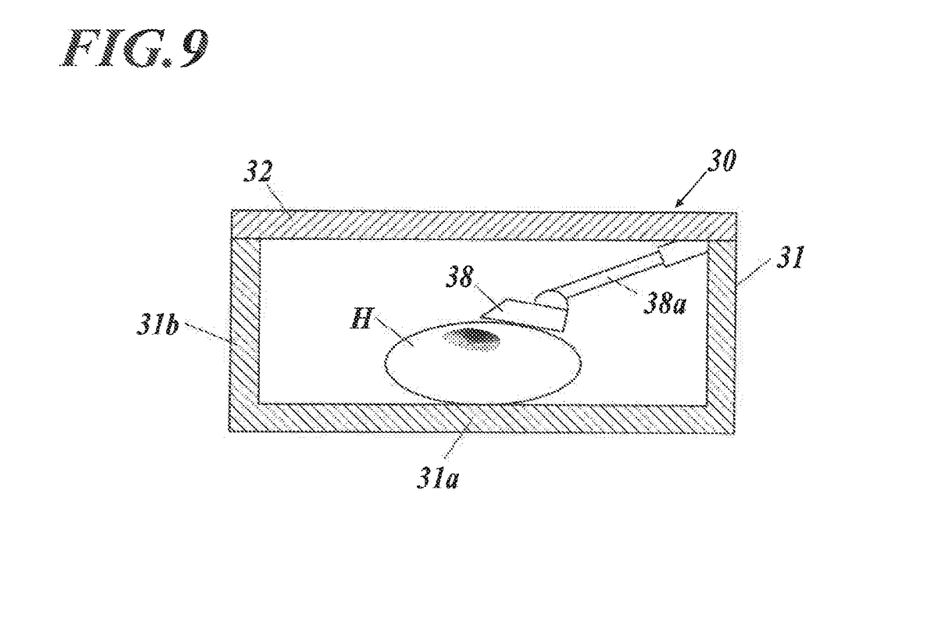
FIG. 9 is a schematic view of the object housing including a heat generator.

As shown in FIG. 9, the object housing 30 in this modification includes a temperature controllable heat generator 38 which is brought into contact with the object H.

The heat generator 38 heats to a high temperature by itself. Being brought into contact with the surface of the object H, the heat generator 38 may heat the surface of the object H or singe the surface depending on the material of the object H.

The heat generator 38 is provided with an arm 38a that holds the heat generator 38, being disposed inside the object H. An angle and distance of the arm 38a relative to the object H is adjustable.

The adjustment of the angle and distance of the arm 38a and the adjustment of the temperature in the heat generator 38 may be automatically controlled by the hardware processor 19 (controller) of the X-ray Talbot imaging apparatus 1 in conjunction with the X-ray Talbot imaging apparatus 1.

In other words, the hardware processor 19 controls the series of imaging performed by the X-ray Talbot imaging apparatus 1 to acquire the plurality of moire images Mo, and at the time of the series of imaging, the hardware processor 19 also may control each operation of the heat generator 38 and the arm 38a.

The heat generator 38 may interfere with X-ray radiation. Therefore, in the X-ray Talbot imaging, it is desirable that the angle and distance of the arm 38a be appropriately adjusted to make the heat generator 38 shifted from the X-ray radiation range. Note that imaging is performed while at least the heat generator 38 is separated from the object H.

According to this modification, the object housing 30 includes the temperature controllable heat generator 38 which is brought into contact with the object H. Therefore, performing the X-ray Talbot imaging leads to clarification of the mechanism of partial changes in physical properties of the object H brought into contact with the heat generator 38. Since such X-ray Talbot imaging is performed without changing an installation environment of the X-ray Talbot imaging apparatus 1, it is possible to prevent troubles in the X-ray Talbot imaging apparatus 1 attributed to the installation environment.

Furthermore, as described in the embodiment, the X-ray Talbot imaging apparatus 1 is preferable in that the X-ray Talbot imaging is performed while the interior of the object housing 30 is set to an environmental condition independent of an external environment and that the object H is imaged under various conditions.

Although embodiments of the present invention have been described and illustrated in detail, the disclosed embodiments are made for purposes of illustration and example only and not limitation. The scope of the present invention should be interpreted by terms of the appended claims The entire disclosure of Japanese patent Application No. 2017-232242, filed on Dec. 4, 2017, is incorporated herein by reference in its entirety.

What is claimed is:

1. An X-ray imaging system comprising:
   an X-ray Talbot imaging apparatus comprising an object table, an X-ray source, a plurality of gratings, and an X-ray detector side by side in a direction of an X-ray radiation axis, wherein the X-ray detector is irradiated with an X-ray from the X-ray source through an object and the plurality of gratings to obtain a moire image required for forming a reconstruction image of the object; and
   an object housing inside which the object is housed and an environmental condition independent of an external environment is set,
   wherein the object housing is provided detachably with respect to the object table.

2. The X-ray imaging system according to claim 1,
   wherein the X-ray Talbot imaging apparatus further includes a hardware processor that causes a series of imaging to acquire the moire image required for forming the reconstruction image of the object, and
   wherein the hardware processor automatically controls setting of the independent environmental condition inside the object housing.

3. The X-ray imaging system according to claim 1, wherein the independent environmental condition includes a condition related to a temperature and/or a humidity inside the object housing.

4. The X-ray imaging system according to claim 1, wherein the object housing includes an X-ray transmitter on the X-ray radiation axis and in an X-ray radiation range around the X-ray radiation axis, the X-ray transmitter being less likely to hinder transmission of an X-ray than a peripheral part.

5. The X-ray imaging system according to claim 1, wherein each grating of the plurality of gratings is a one-dimensional grating.

6. The X-ray imaging system according to claim 5, wherein any one of the object table and the object housing includes a rotator that rotates the object about the X-ray radiation axis.

7. The X-ray imaging system according to claim 1, wherein the X-ray Talbot imaging apparatus and the object housing are provided mechanically independently from each other.

8. The X-ray imaging system according to claim 7, wherein the object housing is provided on the object table so as to be movable back and forth with respect to an X-ray radiation range.

9. The X-ray imaging system according to claim 1, wherein the object housing includes a laser radiator that irradiates the object with a laser beam.

10. The X-ray imaging system according to claim 1, wherein the object housing includes a nail inserter for performing a nailing test on the object.

11. The X-ray imaging system according to claim 1, wherein the object housing includes a temperature controllable heat generator that is made to contact the object.

* * * * *